United States Patent [19]

Clapper

[11] Patent Number: 5,744,515
[45] Date of Patent: Apr. 28, 1998

[54] METHOD AND IMPLANTABLE ARTICLE FOR PROMOTING ENDOTHELIALIZATION

[75] Inventor: David L. Clapper, Shorewood, Minn.

[73] Assignee: BSI Corporation, Eden Prairie, Minn.

[21] Appl. No.: 729,537

[22] Filed: Oct. 11, 1996

Related U.S. Application Data

[63] Continuation of Ser. No. 451,165, May 26, 1995, abandoned.

[51] Int. Cl.$^6$ .................................................. A61L 27/00
[52] U.S. Cl. .................... 523/113; 523/114; 424/423; 623/1; 623/11; 427/2.24; 514/8; 514/21
[58] Field of Search .................... 523/113, 114; 424/423; 427/2.24; 514/8, 21; 623/1, 11

[56] References Cited

U.S. PATENT DOCUMENTS

| | | | |
|---|---|---|---|
| 4,960,423 | 10/1990 | Smith | 623/11 |
| 4,979,959 | 12/1990 | Guire | 623/66 |
| 5,258,041 | 11/1993 | Guire et al. | 604/266 |
| 5,263,992 | 11/1993 | Guire | 623/66 |
| 5,294,551 | 3/1994 | Furcht et al. | 435/180 |
| 5,370,681 | 12/1994 | Herweck et al. | 623/12 |
| 5,563,056 | 10/1996 | Swan et al. | 530/816 |

FOREIGN PATENT DOCUMENTS

| | | | |
|---|---|---|---|
| 9217218 | 10/1992 | WIPO | 623/11 |
| 9321971 | 11/1993 | WIPO | 623/11 |

OTHER PUBLICATIONS

Clapper, D.L., K.M. Hagen, N.M. Hupfer, J.M. Anderson and P.E. Guire, "Covalently Immobolized ECM Proteins Improve Patency and Endotheliazation of 4 MM Grafts Implanted in Dogs", *Tran. Soc. Biiomat.* 16:42 (1993).

Clapper, D.L., S.M. Kirkham and P.E. Guire, "ECM Proteins Coupled to Device Surfaces Improve in vivo Tissue Integration", *J. Cell. Biochem.* 18C:283 (1994).

Golden, M.A., S.R. Hanson, T.R. Kirkman, P.A. Schneider, and A.W. Clowes, "Healing of Polytetrafluoroethylene Arterial Grafts is Influenced by Graft Porosity", *J. Vasc. Surg.* 11:838–845 (1990).

Greisler, H.P., *New Biologic and Synthetic Vascular Prostheses*, R.G. Landes, Co., Austin, Texas (1991).

Hanker, J.S. and B.L. Giammara, "Biomaterials and Biomedical Devices", *Science* 242:885–892 (1988).

Kang, S.S., D. Ren and H.P. Greisler, "Vascular Smooth Muscle Cell Growth on Fibrin Glue Containing Fibroblast Growth Factor–1 and Heparin", *Trans. Soc. Biomat.* 17:33 (1994).

Kinoshita, Y., T. Kuzuhara, M. Kirigakubo, M. Kobayashi, K. Shimura, Y. Okada, "Soft tissue reaction to collagen–immobolized porous polyehtylene: subcutaneous in rats for 20 wk", *Biomaterials*, vol. 14, No. 3, 209–215 (1993).

Kirkham, S.M. and M.E. Dangel, "The Keratoprosthesis: Improved Biocompatability Through Design Through Design and Surface Modification", *Ophth. Surg.* 22: 455–461 (1991).

Kito, H., N. Nakajima and T. Matsuda, "Differentiated Biocompatible Design of Luminal and Outer Graft Surfaces. Photocurable Extracellualr Matrices, Fabrication, and Cellular Response", *ASAIO Journal* 39:M506–M511 (1993).

Kohler, T.R., J.R. Stratton, T.R. Kirkman, K.H. Johansen, B.K. Zierler and A.W. Clowes, "Conventional Versus High–Porosity Polytetrafluoroethlene Grafts: Clinical Evaluation", *Surgery* 112:901–907 (1992).

Kusaba, A., C.R. Fischer, III, T.J. Matulewski, and T. Matsumoto, "Experimental Study of the Influence of Porosity on Development on Neointima in Gore–Tex® Grafts: A Method to Increase Long–term Patency Rate", *Amer. Surg.* 47:347–354 (1981).

Okada, T. and Y. Ikada, "Tissue Ractions to Subcutaneously Implanted, Surface–Modified Silicones", *J. Biomed. Mater. Res.* 27:1509–1518 (1993).

Seeger, J.M. and N. Klingman, "Improved In Vivo Endothlialization of Prosthetic Grafts by Surface Modification with Fibronectin", *J. Vasc. Surg.* 8:476–482 (1988).

Williams S.K., et al, "Adult Human Cell Compatibilty with Prosthetic Graft Material", *J. Surg. Res.* 38:618–629 (1985).

*Primary Examiner*—Andrew E. C. Merriam
*Attorney, Agent, or Firm*—Fredrikson & Byron, P.A.

[57] ABSTRACT

A porous material with an appropriate surface chemistry that promotes capillary endothelialization is disclosed. The material has a porosity that is sufficient to allow capillary endothelialization and a tenaciously bound adhesion molecule that promotes the ingrowth of endothelial cells into the porosity of the material.

44 Claims, No Drawings

METHOD AND IMPLANTABLE ARTICLE FOR PROMOTING ENDOTHELIALIZATION

This application is a continuation of application Ser. No. 08/451,165, filed May 26, 1995, which is now abandoned.

FIELD OF THE INVENTION

This invention relates to the field of biomaterials, implantable medical devices, and cell biology. In particular, the invention relates to methods for improving the performance of medical devices when implanted in a biological environment. In another aspect, the invention relates to devices such as implantable vascular grafts.

BACKGROUND OF THE INVENTION

Biomaterials have long been used in reconstructive surgery to replace diseased or injured organs. Most biomaterials currently used for fabricating implanted devices were originally developed for nonmedical applications. Such materials were initially considered suitable for use in fabricating implant devices if they were nontoxic and had physical properties that would allow the fabrication of desired devices. However, it appears that most if not all commonly used implanted biomaterials have some potential to produce undesirable responses at the material-tissue interface. See, e.g., Hanker, J. S. and B. L. Giammara, "Biomaterials and Biomedical Devices", *Science* 242:885-892 (1988).

Currently, implanted devices are considered successful in situations where any undesirable surface responses that may occur do not unduly affect the host, or significantly interfere with the primary function of the device. For example, the formation of a thrombus layer on the luminal surface does not typically affect the function of a large diameter vascular graft, whereas it may occlude a small diameter graft.

Initial research into the development of materials having improved biocompatibility focused largely on the generation of materials showing minimal reaction with tissue. Although this approach has improved the function of several devices, further improvements in the compatibility and performance of implant devices are desired.

Such improvements may involve the generation of biomaterial surfaces that actually promote desirable tissue interactions, for instance, adhesion and infiltration by specific desirable tissue cells (Hanker et al.). One type of desirable tissue infiltration involves the process known as "endothelialization", which in the case of a vascular graft would involve the migration of endothelial cells from adjacent tissue onto the luminal surface (i.e., the surface lining the lumen) and into the lumen of the graft.

As applied to a vascular graft, for instance, such endothelialization can occur via two different mechanisms (Greisler, H. P., *New Biologic and Synthetic Vascular Prostheses*, R. G. Landes, Co., Austin, Tex. (1991)). One mechanism, termed "transanastomotic" endothelialization, involves promoting pannus ingrowth longitudinally into the graft, from the lumen of the blood vessel into which the graft is inserted. Endothelialization via this method results in endothelial cells lining the lumen of the graft, with few if any endothelial cells in the porosity of the graft.

The other mechanism, termed "transmural" or "transinterstitial" endothelialization, involves promoting the ingrowth of capillaries and/or capillary endothelial cells through the graft wall and into the porosity. Such endothelial cells originate in the microvasculature of adjacent tissue external to the vascular graft, and grow through the vascular graft wall, in part by virtue of its porosity. Under appropriate conditions, the endothelial cells are able to grow through the graft wall and colonize the graft lumen.

The ingrown endothelial cells are often able to then form capillaries within and through the pores of the material forming the vascular graft; however, such capillary formation has not been verified to be an essential component of the process itself. Since the endothelial cells themselves originate from capillaries, and capillaries are often observed within the graft porosity, transmural endothelialization is sometimes also referred to as "capillary endothelialization". The process of capillary endothelialization can be distinguished by its sequential cellular steps, including the initial attachment of endothelial cells to the graft material, followed by their spreading, inward migration, and optionally, proliferation.

Physical approaches for improving endothelialization have tended to concentrate on the surface itself, for instance, the porosity or roughness qualities of the surface. Goldon et. al., for instance, reported that expanded polytetrafluoroethylene ("ePTFE") grafts with an internodal distance of 60 µm provided an optimal porosity to allow transmural endothelialization in baboons. (See Golden, M. A., S. R. Hanson, T. R. Kirkman, P. A. Schneider, and A. W. Clowes, "Healing of Polytetrafluoroethylene Arterial Grafts is Influenced by Graft Porosity", *J. Vasc. Surg.* 11:838-845 (1990).

A similar type of ePTFE graft with the same 60 µm internodal distance was implanted in patients, however, and did not allow endothelialization. (See Kohler, T. R., J. R. Stratton, T. R. Kirkman, K. H. Johansen, B. K. Zierler and A. W. Clowes, "Conventional Versus High-Porosity Polytetrafluoroethylene Grafts: Clinical Evaluation", *Surgery* 112:901-907 (1992)). Applicants have established that the ePTFE grafts implanted in patients were different than those implanted in baboons, in that the ePTFE grafts used with patients were of a modified type employing an outer wrapping of a reinforcing film.

The product known as "Gore-Tex Vascular Graft", for instance, is described as having an average fibril length of 25 microns, in order to allow incorporation of surrounding tissue into the graft implant. This particular product, however, also provides a reinforcing film, integral with the graft outer surface that is said to provide external support for the graft, prevent aneurysmal dilatation, enhance suture retention, and prevent a problematic "zippering" effect. In other experiments transmural endothelialization in dogs was produced by an ePTFE graft in which 800 µm pores were created with a needle; however the porosity was so great that preclotting was required to prevent excessive bleeding. (Kusaba, A., C. R. Fischer, III, T. J. Matulewski, and T. Matsumoto, "Experimental Study of the Influence of Porosity on Development of Neointima in Gore-Tex® Grafts: A Method to Increase Long-term Patency Rate", *Amer. Surg.* 47:347-354 (1981)).

Growth Factors

Apart from physical approaches for achieving endothelialization, certain chemical approaches have been attempted as well. These have tended to concentrate on the use of various proteins, including growth factors and cellular adhesion proteins, or the form of protein attachment to the surface.

Growth factors (GF's) are soluble polypeptides (with molecular weights that typically range from 5 to 50 kilodaltons) that are able to diffuse through the body and stimulate cell division (proliferation). To date it appears that only one type of GF, particularly FGF-1, has been reported to promote capillary endothelialization into a vascular graft. (Greisler, H. P., *New Biologic and Synthetic Vascular Prostheses*, R. G. Landes, Co., Austin, Tex. (1991)). In this report the GF was not immobilized to the device, however, and in fact was provided in a form that would allow it to become solubilized. Specifically, a mixture of fibrin glue, heparin, and FGF-1 was used to fill the interstices of a 60 μm internodal distance ePTFE vascular graft. The graft was subsequently implanted into rabbits and dogs and resulted in improved transmural endothelialization.

It appears that the fibrin glue slowly degraded to release soluble FGF-1, which in turn stimulated the proliferation and migration of endothelial cells to produce capillary endothelialization. In addition to being soluble, FGF-1 has the undesirable secondary effect of promoting the proliferation of smooth muscle cells. These cells also invaded the graft porosity and became hyperplastic in the graft lumen, a result which would not be considered suitable for medical use. Kang, S. S., D. Ren and H. P. Greisler, "Vascular Smooth Muscle Cell Growth on Fibrin Glue Containing Fibroblast Growth Factor-1 and Heparin", *Trans. Soc. Biomat.* 17:33 (1994).

Adhesion Molecules

Adhesion molecules are typically large proteins, carbohydrates or glycoproteins (typically 100 to 1000 kilodaltons) which serve to bind to specific cell surface receptors. In turn, they mechanically attach cells to either a substrate ("surface adhesion molecule", or "SAM") or to adjacent cells ("cell adhesion molecule", or "CAM"). It does not appear that CAM's have been suggested or used for the improvement of capillary endothelialization characteristics in implant devices.

Although a number of SAM proteins have been shown to improve tissue integration with implanted devices (e.g., demonstrating increased fibroblast growth, increased bonding by subcutaneous tissue, decreased inflammation and necrosis of adjacent tissue, and decreased fibrous capsule formation around the implanted devices) it appears that none have been demonstrated to improve capillary endothelialization. See, for example, Okada, T. and Y. Ikada, "Tissue Reactions to Subcutaneously Implanted, Surface-Modified Silicones", *J. Biomed. Mater. Res.* 27:1509–1518 (1993); Kirkham, S. M. and M. E. Dangel, "The Keratoprosthesis: Improved Biocompatability Through Design and Surface Modification", *Ophth. Surg.* 22:455–461 (1991); Clapper, D. L., S. M. Kirkham and P. E. Guire, "ECM Proteins Coupled to Device Surfaces Improve in vivo Tissue Integration", *J. Cell. Biochem.* 18C:283 (1994); and Kito, H., N. Nakajima and T. Matsuda, "Differentiated Biocompatible Design of Luminal and Outer Graft Surfaces. Photocurable Extracellular Matrices, Fabrication, and Cellular Response", *ASAIO Journal* 39: M506–M511 (1993).

Williams et. al. demonstrated that adsorption of several different SAM proteins (including fibronectin and a combination of types I and III collagen) onto vascular grafts improved the in vitro attachment of endothelial cells. The proteins were added for the purpose of evaluating cell seeding, however, and there was no indication of any effect on capillary endothelialization.

Similarly, adsorbed fibronectin was reported by Seeger et al. to produce a slight (i.e., two-fold) increase in the retention of endothelial cells that were added prior to implantation of vascular grafts in to dogs. (See, respectively, Williams S. K. et. al., "Adult Human Endothelial Cell Compatibility with Prosthetic Graft Material", *J. Surg. Res.* 38:618–629 (1985) and Seeger, J. M. and N. Klingman, "Improved In Vivo Endothelialization of Prosthetic Grafts by Surface Modification with Fibronectin", *J. Vasc. Surg.* 8:476–482 (1988)).

Covalent Bonding

Chemical factors have been attached to support surfaces in a variety of ways, including by passive adsorption as described in a variety of the references above. U.S. Pat. Nos. 4,979,959 and 5,263,992 relate to the preparation and use of biocompatible devices, wherein a biocompatible agent is covalently bound, via a photoreactive group within a chemical linking moiety, to a biomaterial substrate.

With regard to SAM's, Kito et. al. (cited above) used photochemistry to coat the outer surface and to fill the porosity of Dacron vascular grafts with gelatin. The luminal surface was then coated with chondroitin sulfate. After implantation in dogs for one week, the grafts showed enhanced fibroblast ingrowth from the outer surface into the graft porosity and no endothelial cells on the luminal surface. No capillary endothelialization was reported.

In another study, adhesion proteins were immobilized by the use of "photochemistry" to the surface of grafts formed from either polyurethane or ePTFE (Clapper, D. L., K. M. Hagen, N. M. Hupfer, J. M. Anderson and P. E. Guire, "Covalently Immobilized ECM Proteins Improve Patency and Endothelialization of 4 MM Grafts Implanted in Dogs", *Trans. Soc. Biomat.* 16:42 (1993)). Applicants have since established that the particular ePTFE graft material was provided in a form as described above, i.e., having an outer wrapping of an external reinforcing film, integral with the graft outer surface, that would serve to greatly reduce wall porosity. The polyurethane, in turn, had few if any pores that extended completely through the graft walls. Using a dog model, both grafts demonstrated various degrees of improved endothelial cell coverage when coated with either fibronectin or type IV collagen, or both. The endothelial cells present on the graft lumen in each case likely migrated from the lumen of the adjacent artery by the process of transanastomic endothelialization. Each type of graft was essentially nonporous and all endothelial cells observed on luminal surfaces of graft were parts of continuous layers of endothelial cells that extended to the lumens of adjacent arteries. Such a pattern of cell growth is consistent with transanastomotic, as opposed to transmural, endothelialization.

Examples have been reported in which covalently immobilized proteins produce improved tissue integration with implant devices. For example, when coupled to silicone rubber (via a combination of corona discharge, graft polymerization and carbodiimide coupling), type I collagen was able to reduce the thickness of fibrous capsules that formed after subcutaneous implantation in rats for 16 weeks (Okada, T. and Y. Ikada, "Tissue Reactions to Subcutaneously Implanted, Surface-Modified Silicones", *J. Biomed. Mater. Res.* 27:1509–1518 (1993)). Type I collagen is thrombogenic, however, and would not be suitable for use with implants such as vascular grafts.

In another experiment, a coating of type IV collagen was photoimmobilized onto silicone rubber breast implants and implanted subcutaneously in pigs for 16 weeks. The coated implants showed greater bonding of tissue to the device surface and thinner fibrous capsules (Clapper, (1994), above). The implants were not described as being porous, however, and no capillary endothelialization was described.

In yet another situation, a coating of type I collagen was applied to a solid polymethylmethacrylate intracorneal lens and implanted in rabbit corneas for 15 months. The implant promoted bonding of stromal tissue, reduced inflammation adjacent to the device, and greatly reduced necrosis of corneal tissue over the device (Kirkham et al., above). Again, the implant was not porous and no capillary endothelialization was described. Lastly, Kinoshita, Y., T. Kuzuhara, M. Kirigakubo, M. Kobayashi, K. Shimura, Y. Okada, "Soft tissue reaction to collagen-immobilized porous polyethylene: subcutaneous implantation in rats for 20 wk", *Biomaterials*, Vol. 14, No. 3, 209–215 (1993) described a polyethylene sheet material having large porosity (400 micron pores), with collagen I covalently coupled by graft polymerization. The material was found to improve tissue ingrowth when implanted subcutaneously into a rat model. The sheet material was not described as having sufficient properties (e.g., unsupported rigidity) for the preparation of a vascular graft, nor was it described as having sufficient porosity for that purpose. Also, and as described above, collagen I would actually be considered unsuitable for use with a vascular graft, in view of its thrombogenic nature.

To date it appears that the art is still in need of materials and related methods for providing an implant surface that is capable of effectively, predictably and reproducibly promoting transmural or capillary endothelialization. It appears that nothing in the art to date suggests or attempts, let alone achieves, the covalent attachment of a suitable adhesion factor to a rigid (e.g., unsupported) porous support surface of an implantable device, in a manner capable of promoting or improving endothelialization into or through the walls of the device.

SUMMARY OF INVENTION

The present invention provides an article comprising an implantable medical device formed of a rigid, porous biomaterial providing a surface bearing an immobilized adhesion molecule in an amount and type suitable to promote capillary endothelialization of the device in vivo.

Applicants have found that in view of the present invention, biomaterials can be provided having the rigidity necessary for the use of an implant in vivo, while at the same time providing the porosity necessary to allow the growth of capillaries through the pores of the biomaterial. Practice of the present invention thereby avoids the conventional need to rely on products such as porous ePTFE having an outer reinforcing film for use in vascular grafts. Instead, the invention allows the use of porous ePTFE itself, modified only by the immobilized adhesion molecules described herein.

In a particularly preferred embodiment, the article is in the form of a vascular graft and the biomaterial is selected from the group consisting of tetrafluoroethylene polymers (such as ePTFE), aromatic/aliphatic polyester resins (such as polyethylene terephthalate ("PET") and poly(butylene terephthalate) ("PBT"), polyurethanes, and silicone rubbers (such as heat cured rubbers and those formed from "room temperature vulcanizing" (RTV) silicone elastomers). In a further preferred embodiment, the adhesion molecule is selected from the group consisting of fibronectin, laminin, and collagen. Vascular grafts of the invention exhibit performance characteristics that closely approximate those of natural vessels, e.g., in terms of integrity, strength, and endothelial cell coverage.

In a further preferred embodiment the vascular graft is formed from ePTFE having pores extending through the graft wall, and exhibiting on the order of 10 to 300 um internodal distance, as determined by scanning electron microscopy. In such an embodiment, the adhesion molecules are covalently immobilized to the surface, including the pore surfaces, of the implant by means of photochemistry.

Vascular grafts of the present invention have been found to promote significantly improved endothelialization when evaluated in vivo. Such improvement can be expressed in terms of either the number of cells found to colonize pore surfaces and the interior surface of the biomaterial, and/or in terms of the speed of endothelialization upon contact with the body. Preferred grafts demonstrate on the order of three-fold or greater improvement in either or both respects as compared to uncoated controls, and preferably four-fold or greater. As compared to other known techniques, these results represent significant improvement.

In another aspect, the invention provides a method of preparing an implantable medical device; an implantable medical device preparable by such a method; and an implantable medical device prepared by such a method. The device can be formed either by pretreating a biomaterial with adhesion molecules and then fabricating the device from the treated biomaterial, or by first fabricating the device and then treating the exposed surfaces of the device. In a preferred embodiment, the method comprises the steps of:

(a) providing an implantable device formed of a porous, rigid biomaterial providing a tissue contacting surface;

(b) contacting the surface with adhesion molecules bearing one or more latent photoreactive groups; and (c) activating the photoreactive groups in order to immobilize the adhesion molecules to the surface.

In a further aspect, the invention provides a method of promoting endothelialization in an implanted medical device, the method comprising the steps of;

(a) providing a implantable device formed of a porous, rigid biomaterial providing a tissue contacting surface;

(b) contacting the surface of the biomaterial with adhesion molecules bearing one or more photoreactive groups;

(c) activating the photoreactive groups in order to immobilize the adhesion molecules to the surface, and (d) implanting the device in contact with bodily tissues or fluids.

DETAILED DESCRIPTION OF THE INVENTION

The present invention provides an article comprising an implantable medical device formed of a porous, rigid biomaterial that provides a surface bearing an immobilized adhesion molecule in an amount and type suitable to promote capillary endothelialization through the surface and into the device when used in vivo.

As used herein, the following terms and words shall have the following ascribed meanings:

"implantable medical device", which for brevity will be referred to as a "device" or a "medical device", will refer to an object fabricated, at least in part, from a biomaterial and intended for use in contact with bodily tissues, including bodily fluids;

"biomaterial" shall refer to the chemical composition of the material used to prepare a device, and which provides one or more of its tissue contacting surfaces;

"porosity", and inflections thereof (such as "pores" and "porous"), shall refer to a biomaterial having small channels or passages which start at an external (e.g., first major)

surface of the biomaterial and extend substantially through the biomaterial to an internal (e.g., second major) surface;

"rigid" and inflections thereof, will refer to the ability of a particular biomaterial, when fabricated in the form of an implantable medical device, to withstand the pressures encountered in the course of its use, e.g., to retain patency and pore structure in vivo;

"surface" shall refer to the interface between the biomaterial and its environment. The term is intended to include the use of the word in both its macroscopic sense (e.g., the two major faces of a sheet of biomaterial), as well as in its microscopic sense (e.g., the lining of pores traversing the material). The surface is capable of serving as an immobilization site for cell adhesion molecules, as well for the attachment and migration of endothelial cells;

"adhesion molecules" shall refer to peptides, proteins and glycoproteins capable of binding to a substrate and/or cells in order to attach cells to the substrate or to adjacent cells;

"endothelialization" will, unless otherwise specified, be used interchangeably with the phrase "capillary endothelialization" to refer to the growth of endothelial cells on substantially all tissue contacting surfaces of a biomaterial used to form a porous, rigid device.

Devices

Devices of the present invention include medical devices intended for prolonged contact with bodily fluids or tissues, and in particular, to those devices that can benefit from the capillary endothelialization when used in either in vivo or in vitro applications.

Preferred devices are implantable in the body, and include vascular grafts and artificial organs, such as the pancreas, liver, and kidney. Other suitable implant devices include, but are not limited to, devices used to implant genetically modified cells that deliver recombinant proteins for therapeutic use, and artificial tissue or organ implants, such as replacement skin, joints, and ears.

The significance of capillary endothelialization will vary with each particular device, depending on the type and purpose of the device. Ingrown capillaries can be useful for providing perfusion into the device, e.g., to carry nutrients to cells in the device and to carry away waste products. Ingrown capillaries can also be useful for providing endothelial cells to line the surfaces of vascular grafts to improve blood compatibility.

Other suitable devices are capable of in vitro use, such as those used for the generation of tissue engineered organs. In the course of a tissue engineering process, for instance, an external device can serve as a scaffolding structure for the culture of cells which, in turn, will migrate, proliferate and differentiate to form tissues or organs, which are subsequently implanted in patients.

Biomaterials

Devices of the present invention can be prepared from a variety of rigid biomaterials capable of providing a surface for the adhesion and migration of endothelial cells. A wide variety of suitable materials can be employed as the support, primary considerations being that they provide an optimal combination of such properties as strength, surface area, ease of preparation and use, and cost.

Preferred support materials are synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyl acetate; polymers formed of ethylene, propylene, and tetrafluoroethylene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Other suitable support materials include metals and ceramics. The metals include, but are not limited to, titanium, stainless steel, cobalt chromium. The ceramics include, but are not limited to, silicon nitride, silicon carbide, zirconia, and alumina, as well as glass and silica. ePTFE is a preferred biomaterial for use in fabricating implantable devices of the present invention, and particularly for fabricating vascular grafts. Suitable ePTFE is available in the form of vascular grafts from such sources as IMPRA, Inc., Tempe, Ariz. The commercially available grafts are constructed of ePTFE and supplied in sterile form in a variety of configurations, including straight, tapered and stepped configurations.

Such products are known to be biologically inert, are able to prevent significant inflammatory response, and can be prepared to have a controlled microporous structure. Such biomaterials can be characterized in a number of ways, including by fibril length. Control of fibril length, in turn, can be used to produce microstructures that are capable of excluding or accepting tissue ingrowth.

Rigidity and Porosity

Preferred biomaterials are those that provide sufficient rigidity for their intended purposes, whether used in vivo or in vitro. For use in forming a vascular graft, for instance, a biomaterial will be of sufficient rigidity to allow the graft to retain graft patency and pore structure in the course of its intended use.

Rigidity of a biomaterial can be evaluated by any suitable means. The nodal regions of ePTFE are composed of nonporous PTFE that serves to provide tear resistance (e.g., for sutures and resistance to aneurysmal dilatation). The internodal regions are composed of fibers of PTFE which serve to connect the nodes, with the spaces between the fibers providing the porosity referred to herein. The nodal size can be expressed as the percentage of the tissue contacting surface that is composed of nodal PTFE.

The distance between nodes can be expressed as the average fibril length. In turn, the porosity is commonly expressed as the internodal distance (i.e., the average distance from the middle of one node to the middle of the adjacent node). Preferred ePTFE materials have nodes of sufficient size and frequency to provide adequate strength (e.g., with respect to aneurysmal dilatation) and internodal regions of sufficient frequency and fiber length to provide adequate porosity (to allow for capillary endothelialization). Such an ePTFE material is one that provides nodes that comprise on the order of 30% or more, and preferably 40% or more of the tissue contacting surface.

Such materials will provide fewer, though thicker nodes, which in turn will confer significantly greater strength in vivo. Given the present specification, those skilled in the art will be able to identify and fabricate devices using biomaterials having a suitable combination of porosity and rigidity.

Biomaterials are preferably suitably porous to allow the attachment and migration of cells, which may be followed by the formation and growth of capillaries into the surface. Suitable pores can exist in the form of small channels or passages which start at an external surface and extend partially or completely through the biomaterial. In such cases, the cross-sectional dimensions of the pores are larger than the diameter of a capillary (5 μm) and are typically less than 1 mm. Interconnecting pores are preferable to pits (nonconnecting pores).

Preferably, in turn, the average diameter of such pores ranges from about 5 μm to about 1 mm. The porosity must be sufficiently large to allow capillary endothelialization; therefore the average diameter of individual pores should be greater than about 5 μm. The upper pore size value is not critical so long as the biomaterial retains sufficient rigidity, however, it is unlikely that a useful device would have an average pore size of greater than about 1 mm. Such pore dimensions can be quantified by microscopic examination.

With a preferred biomaterial such as an ePTFE material the porosity can be determined for the internodal areas of the material. The internodal distance and the node widths are also useful factors, not only in determining the overall porosity, but in determining the strength of the material as well.

Adhesion Molecules

Suitable adhesion molecules are typically large, naturally occurring proteins or carbohydrates, with molecular weights above 100,000 daltons. In vivo, adhesion molecules are typically able to bind to specific cell surface receptors, and mechanically attach cells to the substrate or to adjacent cells. In addition to promoting cell attachment, suitable adhesion molecules can promote other cell responses including cell migration and cell differentiation (which in turn can include the formation of capillary tubes by endothelial cells).

Preferred adhesion molecules for use in the present invention include substrate adhesion molecules (SAM's) such as the proteins laminin, fibronectin, collagen, vitronectin, and tenascin, and adhesion peptides or functional synthetic analogs derived from SAM's. Other suitable adhesion molecules include cell to cell adhesion molecules (CAM's) such as N-cadherin and P-cadherin.

Parent (i.e., native) adhesion proteins typically have one or more active peptide domains that bind to cell surface receptors and produce the cell attachment, migration, and differentiation activities of the parent adhesion proteins. These domains consist of specific amino acid sequences, several of which have been synthesized and reported to promote the adhesion of endothelial cells. These domains and functional analogs of these domains are termed adhesion peptides. Desirably, adhesion peptides used in this invention have between about 3 and about 30 amino acid residues in their amino acid sequences.

Adhesion peptides from fibronectin include, but are not limited to, RGD (arg-gly-asp), REDV (arg-glu-asp-val), and C/H-V (WQPPRARI or trp-gln-pro-pro-arg-ala-arg-ile). Adhesion peptides from laminin include, but are not limited to, YIGSR (tyr-ile-gly-ser-arg) and SIKVAV (ser-ile-lys-val-ala-val) and F-9 (RYVVLPRPVCFEKGMNYTVR or arg-tyr-val-val-leu-pro-arg-pro-val-cys-phe-glu-lys-gly-met-asn-tyr-thr-val-arg). Adhesion peptides from type IV collagen include, but are not limited to, Hep-III (GEFYFDLRLKGDK or gly-glu-phe-tyr-phe-asp-leu-arg-leu-lys-gly-asp-lys).

See, for example, the following disclosures, each of which are incorporated herein by reference: Kleinman, H. K, B. S. Weeks, H. W. Schnaper, M. C. Kibbey, K. Yamamura and D. S. Grant, "The Laminins: A Family of Basement Membrane Glycoproteins Important in Cell Differentiation and Tumor Metastases", *Vitamins and Hormones* 47:161-186 (1993); Hubbell, J. A., S. P. Massia and P. D. Drumheller, "Surface-grafted Cell-binding Peptides in Tissue Engineering of the Vascular Graft", *Ann. N. Y. Acad. Sci.* 665:253-258 (1992); Mooradian, D. L., J. B. McCarthy, A. P. N. Skubitz, J. D. Cameron and L. T. Furcht, "Characterization of FN-C/H-V, a Novel Synthetic Peptide from Fibronectin that Promotes Rabbit Corneal Epithelial Cell Adhesion, Spreading, and Motility", *Invest. Ophth. & Vis. Sci.* 34:153-164 (1993); Charonis, A. S., A. P. N. Skubitz, G. G. Koliakos, L. A. Reger, J. Dege, A. M. Vogel, R. Wohlhueter and L. T. Furcht, "A Novel Synthetic Peptide from the B1 Chain of Laminin with Heparin-binding and Cell Adhesion-promoting Activities, *J. Cell Biol.* 107:1253-1260 (1988), and Koliakos, G. G, K. Kouzi-Koliakos, L. T. Furcht, L. A. Reger and E. C. Tsilibary, "The Binding of Heparin to Type IV Collagen: Domain Specificity with Identification of Peptide Sequences from the α1(IV) and α2(IV) Which Preferentially Bind Heparin", *J. Biol. Chem.* 264:2313-2323 (1989).

The density of adhesion molecules carried by the device's supporting surface should be sufficient to promote endothelial cell adhesion and migration. This density can be provided in the form of a plurality of different molecule types and/or a plurality of molecules of a particular type. RGD, for instance, is capable of promoting endothelial cell attachment and spreading when immobilized at 0.001 femtomoles ($10^{-18}$ moles) per square centimeter. This is the minimum desirable density of adhesion molecules (see, e.g., Massia, S. P. and J. A. Hubbell, "An RGD Spacing of 440 nm Is Sufficient for Integrin $\alpha_v\beta_3$-mediated Fibroblast Spreading and 140 nm for Focal Contact and Stress Fiber Formation", *J. Cell Biol.* 114:1089-1100 (1991). Also, a much higher density is required to generate coatings produced by crosslinking adjacent adhesion molecules. This approach requires 1 to 10 monolayers of adhesion molecules on the supporting surface, which would be about $10^{-10}$ to $10^{-9}$ moles of peptide or $10^{-12}$ to $10^{-11}$ moles of protein per square centimeter. Therefore, the density of adhesion molecules will desirably range from about $10^{-18}$ to about $10^{-9}$ moles of adhesion molecules per square centimeter of biomaterial surface.

Immobilization

Preferably, the adhesion molecules are covalently bound to the porous device by either of two approaches. In one embodiment, the adhesion molecules are covalently bonded to the biomaterial surface. In an alternative embodiment, the adhesion molecules are covalently bound to adjacent adhesion molecules in a manner that produces a crosslinked network of adhesion molecules, with the network being physically entrapped within the interconnecting porosity of the biomaterial. Preferred devices provide the attached adhesion molecules in a form that provides effective activity after implantation or in the cell culture conditions described above. Desirably, the covalent bonding with either approach is achieved with latent reactive groups.

In the embodiment in which adhesion molecules are covalently bound to the biomaterial surface, the molecules are desirably covalently linked to the surface through a linking group, the linking group including the residue of a latent reactive group employed to covalently bond to the surface.

In another preferred embodiment, the coating of adhesion molecule is generated by covalent linkage of adjacent adhesion molecules, resulting in a network of crosslinked adhesion molecules being physically entrapped within the biomaterial porosity.

Preferably, an adequate density of adhesion molecule is uniformly and homogeneously distributed on the material surfaces to provide a continuous surface of adhesion molecule upon which endothelial cells can attach and migrate.

The term "latent reactive group" as used herein, refers to a chemical group that responds to a specific applied external energy source in order to undergo active specie generation, resulting in covalent bonding to an adjacent molecule or biomaterial surface. Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive" being particularly preferred.

Latent reactive groups respond to specific applied external stimuli to undergo active specie generation with resultant covalent bonding to an adjacent chemical structure, e.g., as provided by the same or a different molecule. Latent reactive groups are those groups of atoms in a molecule that retain their covalent bonds unchanged under conditions of storage but that, upon activation by an external energy source, form covalent bonds with other molecules. The latent reactive groups generate active species such as free radicals and particularly nitrenes, carbenes, and excited states of ketones upon absorption of external electric, electromagnetic or kinetic (thermal) energy. Latent reactive groups may be chosen to be responsive to various portions of the electromagnetic spectrum, and latent reactive groups that are responsive to e.g., ultraviolet and visible portions of the spectrum are preferred and are referred to herein occasionally as "photochemical" groups.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of latent reactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of latent reactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate.

Other latent reactive groups include the aliphatic azo compounds such as azobisisobutyronitrile, the diazirines (—$CHN_2$) such as 3-trifluoromethyl-3-phenyldiazirine, the ketenes (—CH=C=O) such as ketene and diphenylketene. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

Upon activation of the latent reactive groups, the coating adhesion molecules are covalently bound to each other and/or to the material surface by covalent bonds through residues of the latent reactive groups. Exemplary latent reactive groups, and their residues upon activation, are shown as follows.

| Latent Reactive Group | Residue Functionality | |
|---|---|---|
| aryl azides | amine | R-NH-R' |
| acyl azides | amide | R-CO—NH-R' |
| azidoformates | carbamate | R-O—CO—NH-R' |
| sulfonyl azides | sulfonamide | R-$SO_2$—NH-R' |
| phosphoryl azides | phosphoramide | $(RO)_2PO$—NH-R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |
| dialkyl peroxides | ethers | |
| diacyl peroxides | esters and new C—C bonds | |
| peroxyesters | ethers, esters, and new C—C bonds | |

Adhesion molecules useful in the invention desirably have an average of at least two and preferably three or more latent reactive groups per adhesion molecule. Crosslinking between adjacent molecules may be formed through the use of adhesion molecules each having two or more latent reactive groups. Such crosslinking aids in the retention of adhesion molecules within the porosity of devices.

Endothelialization

The ability of a surface to promote capillary endothelialization can be determined in any suitable manner, either in vivo or in vitro. A preferred determination is accomplished by performing an assay known as the rat "fat pad" assay, as described herein. Using an in vivo assay, endothelialization will typically be evaluated for a particular biomaterial and device—both with and without immobilized adhesion molecule. It has been found that implantable devices without a coating of the present invention will demonstrate little or no capillary endothelialization. In comparison, devices of the present invention typically demonstrate two-fold or more, and preferably three-fold or more, increase in the number of endothelial cells or capillaries present on the tissue contacting surfaces (including pores) of a biomaterial, as compared to an uncoated control.

The present invention improves endothelialization into devices by coating the material surface with a plurality of adhesion molecules. As described above, capillary endothelialization into a porous device involves conditions intended to promote the migration of endothelial cells into the porosity, the proliferation of the endothelial cells, with or without the formation into the tubular structure of capillaries.

The invention is further illustrated by the following nonlimiting examples.

EXAMPLES

Example 1
Immobilization of Adhesion Molecules

As described in greater detail below, three adhesion molecules (fibronectin, laminin, and type IV collagen) were obtained from commercial sources and photoderivatized by covalent attachment of a photoactivatible latent reactive group. The proteins were then added to a porous vascular graft device formed from expanded polytetrafluoroethylene (ePTFE). The proteins were illuminated to activate the photoactivatible latent reactive groups and produce covalent immobilization to the ePTFE device.

ePTFE has a low content of abstractable hydrogens; therefore, the mechanism of photoimmobilizing the adhesion molecules to ePTFE is believed to occur primarily via crosslinking of adjacent adhesion molecules. In turn, the covalently crosslinked network of adhesion molecules is immobilized via physical entrapment within the porosity of the ePTFE.

Materials.

Human serum fibronectin was obtained from Alpha Therapeutic Corporation, Los Angeles, Calif. Laminin produced from the Engelbreth-Holm-Swarm mouse tumor cell line was obtained from Collaborative Biomedical Products, Bedford, Mass. Human placental type IV collagen was obtained from Sigma Chemical Co., St. Louis, Mo. ePTFE vascular grafts with an internal diameter of 6 mm or 10 mm, a wall thickness of about 0.3 mm to about 0.4 mm, an internodal distance of 30 µm, and no external wrapping were obtained from IMPRA, Inc., Tempe, Ariz. A graft material identified as product "80S10TW" (80 cm length, 10 mm inner diameter, straight, thinwall) was used to prepare and evaluate coated discs as described below.

Synthesis of heterobifunctional crosslinking agent.

A heterobifunctional crosslinking agent (BBA-EAC-NOS) was synthesized and used to photoderivatize each protein. The BBA-EAC-NOS has a benzophenone photoactivatible group on one end (benzoyl benzoic acid, BBA), a spacer in the middle (epsilon aminocaproic acid, EAC), and an amine reactive thermochemical coupling group on the other end (N-oxysuccinimide, "NOS"). BBA-EAC was synthesized from 4-benzoylbenzoyl chloride and 6-aminocaproic acid. Then the NOS ester of BBA-EAC was synthesized by esterifying the carboxy group of BBA-EAC by carbodiimide activation with N-hydroxysuccimide to yield BBA-EAC-NOS.

Photoderivatization and radiolabelling of adhesion molecules.

Fibronectin, laminin, and type IV collagen were each photoderivatized by covalently coupling primary amines on the proteins via the NOS ester of BBA-EAC-NOS. The BBA-EAC-NOS was added at a ratio of 10–15 moles of BBA-EAC-NOS per mole of protein.

Following photoderivatization, an aliquot of each photoderivatized protein was radiolabelled with tritium for use in quantitating the amount of protein that was photoimmobilized onto the ePTFE. The radiolabelling procedure consisted of first adding one mole of formaldehyde per five moles of amine on each protein. The resulting Schiff base was then reduced with one mole of sodium borohydride (4–20 curies per millimole) per 20 moles of amine on the protein. Excess radiolabel was removed by dialysis.

Covalent bonding of photoderivatized adhesion molecules to ePTFE.

Solutions of photoderivatized proteins were added to ePTFE, allowed to adsorb for 2 hours at room temperature, and illuminated at 320 to 340 nm to activate the BBA moieties and produce covalent coupling. Laminin and fibronectin were added at 25 µg protein per square centimeter of ePTFE, and type IV collagen was added in at 100 µg protein per square centimeter of ePTFE. Following illumination, uncoupled proteins were removed by washing the samples overnight in phosphate buffered saline (PBS) containing 1% Tween 20. After the PBS/Tween 20 wash, the samples were sterilized by soaking 20 minutes in 70% ethanol. The residual Tween 20 and ethanol were then removed by washing in sterile PBS.

Immobilized levels of proteins on ePTFE.

Tritium labelled proteins were used to quantitate immobilized levels of each protein on ePTFE, with each tritiated protein being applied either after being photoderivatized (to quantitate the amount of protein immobilized via photoimmobilization) or before being photoderivatized (to quantitate the amount of protein immobilized via adsorption). As is shown in Table 1, higher levels of each protein were immobilized via photochemistry than via adsorption, with the respective differences being 2.5 fold higher with laminin, 14-fold higher with type IV collagen, and 1.6-fold higher with fibronectin. Under these conditions, the percentage of each added photo-protein that was photoimmobilized (% coupling efficiency) ranged from 2.0 to 9.4.

TABLE 1

Levels of tritiated adhesion molecules immobilized onto ePTFE. Immobilized protein levels are shown as the mean of 3 replicates; S.E.M. indicates the standard error of the mean.

| Protein coating | Applied protein µg/sq. cm. | Immobilized protein µg/sq. cm. | S.E.M. | % Coupling Efficiency |
|---|---|---|---|---|
| Laminin | 25 | 0.95 | 0.12 | 3.8 |
| Photo-laminin | 25 | 2.34 | 0.71 | 9.4 |
| Type IV collagen | 100 | 0.24 | 0.02 | 0.24 |
| Photo-type IV collagen | 100 | 3.45 | 0.49 | 3.4 |
| Fibronectin | 25 | 0.32 | 0.04 | 1.3 |
| Photo-fibronectin | 25 | 0.50 | 0.05 | 2.0 |

Example 2
Cell Culture Evaluations

In vitro biological activity of immobilized adhesion molecules.

ePTFE disks 1.4 cm in diameter were coated with non-tritiated photoderivatized proteins using the protocol described above. They were then evaluated for in vitro biological activity in an assay to determine their ability to support the proliferation of vascular endothelial cells. Uncoated ePTFE disks were evaluated as controls and the remaining disks were coated with either laminin, type IV collagen or fibronectin. Each of the four types of disks were placed into individual wells of 24-well cell culture plates, seeded with 1500 cells per well of calf pulmonary endothelial cells (CPAE cells obtained from the American Type Culture Collection, Rockville, Md.), and cultured under standard cell culture conditions set forth by the American Type Culture Collection.

After six days in culture, the relative number of cells in each well was determined using a tetrazolium metabolic dye. When the tetrazolium dye (MTT) is added to cells, the metabolic activity of living cells converts the added MTT to a colored product, with the amount of color generation being proportional to the number of viable cells being present. Since the colored product of MTT metabolism absorbs light at 570 nm, the relative number of cells growing on each ePTFE disk could be quantified by solubilizing the cells on each disk and measuring the absorbance of the resulting solution in a spectrophotometer at 570 nm as described by Mosmann, T., "Rapid Colorimetric Assay for Cellular Growth and Survival: Application to Proliferation and Cytotoxicity Assays", J. Immunol. Method. 65:55–63 (1983).

Table 2 shows that ePTFE coated with each type of protein supports on the order of 19 fold or more numbers of endothelial cells, as compared to an uncoated control. It can be noted that each photo-immobilized protein promotes a similar level of endothelial cell growth, which is consistent with results reported by others as is described above.

TABLE 2

Growth of endothelial cells on ePTFE previously coated with photoimmobilized proteins. Relative cell numbers are expressed in terms of the absorbance of a tetrazolium dye (MTT) measured at 570 nm, with the mean of 4 replicates and standard error of the mean (S.E.M.) being shown.

| Protein coating | MTT absorbance at 570 nm | |
|---|---|---|
| | mean | S.E.M. |
| Uncoated | 0.008 | 0.004 |
| Photo-laminin | 0.153 | 0.002 |
| Photo-collagen | 0.158 | 0.007 |
| Photo-fibronectin | 0.153 | 0.006 |

Similar experiments were performed to directly compare the growth of CPAE cells on ePTFE previously coated with adsorbed or photoimmobilized proteins. The immobilized levels of fibronectin and collagen were similar to those reported in Table 1, and the coated ePTFE samples were evaluated for growth of CPAE cells as is described for Table 2. The cell growth results unexpectedly showed that the level of cell growth found with adsorbed proteins was not statistically different than that observed for uncoated samples. In contrast, the photoimmobilized proteins consistently promoted CPAE growth that was greater than the uncoated controls, and comparable to that observed with the photoimmobilized proteins in Table 2. While not intending to be bound by theory, it appears that the adsorbed proteins were removed from the ePTFE by the CPAE cells, thus producing a surface that was comparable to that of uncoated ePTFE. In contrast, the covalently immobilized (photoimmobilized) proteins were not removed by the CPAE cells and provided a stable surface for cell growth. Moreover, the improved stability of such covalently immobilized proteins is expected to similarly improve the stability of such coatings after being exposed to the rigors of the in vivo environment.

Example 3

Capillary endothelialization into Coated ePTFE in the Rat Model

Rat epididymal fat pad implant system.

Applicants have found that adhesion molecules of the present invention should be strongly, e.g., covalently, bound to a substrate in order to promote endothelialization into porous implant devices. In order to more closely approximate the level of endothelialization necessary for human applications, and in turn predict the performance of various embodiments, a suitable animal implant system can be used. Most devices for which the invention is likely to be used in patients (e.g., vascular grafts) are implanted at subcutaneous or similar sites. Such sites typically possess large amounts of adipose tissue. In turn, often 90% or more of the cells present in such adipose tissue are microvascular endothelial cells, with most of the remaining cells being adipose cells (See, e.g., Williams, S. K., T. F. Wang, R. Castrillo and B. E. Jarrell, "Liposuction-derived Human Fat Used for Vascular Graft Sodding Contains Endothelial Cells and Not Mesothelial Cells as the Major Cell Type", J. Vasc. Surg. 19:916–923 (1994).

In contrast to humans, subcutaneous sites in animals typically contain little adipose tissue, few microvascular endothelial cells, and numerous fibroblasts (Williams, S. K. and L. B. Kleinert, "Differential Healing of ePTFE Implants in Subcutaneous Versus Adipose Tissue", pp 74–75 in Symposium Notebook for Surfaces in Biomaterials Symposium held in Scottsdale, Ariz. (Sep. 7–10, 1994). However, rat epididymal fat has a morphology that closely resembles human subcutaneous fat in cellular content. Moreover, microvascular endothelial cells from rat epididymal fat pads can be isolated and cultured using procedures similar to those used for microvascular endothelial cells from human subcutaneous adipose tissue. Following is a protocol developed by Dr. Stuart Williams of the University of Arizona at Tucson, and incorporated herein for the evaluation of coated devices of the present invention in an animal model.

Implant protocols.

Eighteen adult Sprague Dawley rats were implanted with 1 cm diameter disks of ePTFE coated in the manner described for Table 2. Also, four sample types as described in Table 2 were evaluated, namely, uncoated controls and each of the three photoimmobilized proteins (laminin, type IV collagen, and fibronectin). For the implant surgery, each rat was anesthetized with 50 mg/kg Nembutal®, a midline abdominal incision was made, and the distal portion of each epididymal fat pad was surgically exposed. The serosal layer of each fat pad was cut, and one ePTFE disk was inserted into each fat pad; therefore each rat received two ePTFE disks. The ePTFE disks were immobilized by suturing the fat around each disk, and the abdominal incisions were closed.

Each of the four coating variations was implanted into 9 different rats, with the two variations implanted in each rat being randomized. Six rats (containing 3 disks with each coating variation) were terminated at 1, 3, and 5 weeks, respectively. The disks and surrounding epididymal tissue were explanted and prepared for histology and immunocytochemistry.

Histology.

Each sample of ePTFE and surrounding tissue was fixed with 4% paraformaldehyde in phosphate buffered saline (pH 7.4), embedded in paraffin, sectioned, deparaffinized, and stained to allow visualization of the cells growing in the porosity of the ePTFE. Sections stained with hematoxylin and eosin (H&E) showed large numbers of capillaries in ePTFE disks coated with fibronectin or laminin; however fewer capillaries were observed in disks coated with type IV collagen or uncoated control disks.

Since H&E cannot be used to distinguish between endothelial cells and several other cell types, an immunocytochemical stain specific for vascular endothelial cells was used to verify that the structures that appeared to be capillaries (based on the H&E staining) were indeed composed of endothelial cells. An immunocytochemical procedure was employed that relied on the presence of a unique cell-surface carbohydrate within vascular endothelial cells that can be stained by the lectin Griffonia (See, e.g., Christy, J. P., F. M. Lupinetti, A. H. Mardan and S. A. Thompson, "Endothelial Cell Viability in the Rat Aortic Wall", *Ann. Thorac. Surg.* 51:204–207 (1991).

The staining procedure involved reacting the tissue sections with fluorescein-labelled Griffonia and using a fluorescence microscope to identify the cells that show fluorescence. For this study, the fluorescent group on the Griffonia was fluorescein isothiocyanate (FITC). The staining with fluorescein-labelled Griffonia produced two significant results. First, the assay confirmed that the tube-like structures that appeared to be capillaries when evaluated with H&E staining were indeed composed of endothelial cells. The relative numbers of capillaries present in uncoated disks versus those with each protein coating are shown in Table 3, and show that 3 to 4 times as many capillaries grew into ePTFE coated with fibronectin or laminin than into uncoated disks or disks coated with type IV collagen.

Second, the assay confirmed the presence of additional endothelial cells that had not formed capillaries, as well as many other endothelial cells that were present in the porosity of ePTFE disks coated with type IV collagen but not in control (uncoated) disks or in disks coated with fibronectin or laminin.

The data supports the conclusion that: 1) uncoated ePTFE disks promoted the ingrowth of few endothelial cells and few capillaries, 2) ePTFE disks coated with type IV collagen promoted the ingrowth of endothelial cells, but most of these endothelial cells did not form capillaries, and 3) ePTFE disks coated with fibronectin or laminin promoted the ingrowth of endothelial cells with a significant level of capillary formation.

TABLE 3

Ingrowth of capillaries into coated ePTFE samples implanted in rat fat pads for 5 weeks. Capillary tubes were counted in microscope fields of 400 × 400 microns (0.16 sq. mm) and converted from numbers per 0.16 sq. mm to numbers per 1 sq. mm. Means are the averages of 5 to 9 determinations. S.E.M. is the standard error of the mean.

| Protein coating | Capillary tubes per sq. mm. | |
| --- | --- | --- |
| | mean | S.E.M. |
| Uncoated | 31.2 | 5.1 |
| Photo-laminin | 95.6 | 5.3 |
| Photo-collagen | 30.0 | 6.1 |
| Photo-fibronectin | 138 | 19.4 |

Since capillary endothelialization into the walls of a graft is a key component in the process of in vivo transmural endothelialization, coatings that are capable of promoting capillary endothelialization into ePTFE disks implanted in rat epididymal fat pats can be expected to promote transmural endothelialization of interpositional grafts implanted in arteries.

The Examples demonstrate that adhesion proteins can be covalently bound to ePTFE at levels considerably higher than that observed with simple adsorption. They show also that each photoimmobilized protein produced a similar 19 fold enhancement in endothelial cell growth in vitro. Finally, the Examples demonstrate that fibronectin and laminin, but not type IV collagen, produce significantly enhanced capillary endothelialization in vivo.

While a preferred embodiment of the present invention has been described in these Examples, it should be understood that various changes, adaptations and modifications may be made therein without departing from the spirit of the invention and the scope of the appended claims.

What is claimed is:

1. An article comprising an implantable medical device comprising a rigid, porous biomaterial selected from the group consisting of non-soluble synthetic polymers, metals and ceramics and providing a surface bearing immobilized adhesion molecules selected from the group consisting of fibronectin, laminin, collagen, and active peptide domains thereof, the adhesion molecules having been bound to each other or the surface of the biomaterial by the activation of one or more photoreactive groups covalently bound to the adhesion molecules, the photoreactive groups having been selected from the group consisting of photoreactive aryl ketones, azides, diazirines, ketenes and diazo compounds, the adhesion molecules being provided directly upon the surface in an amount suitable to promote capillary endothelialization of the device in vivo, wherein the adhesion molecule is capable of binding to the surface of a cell, and wherein the biomaterial is porous in that it provides channels or passages extending through the biomaterial and of sufficient dimensions to permit the growth of capillaries therethrough.

2. An article according to claim 1 wherein the biomaterial provides pores having an average diameter from about 5 microns to about 1 mm.

3. An article according to claim 2 wherein the biomaterial is selected from the group consisting of tetrafluoroethylene polymers, aromatic/aliphatic polyester resins, polyurethanes, and silicone rubbers.

4. An article according to claim 3 wherein the tetrafluoroethylene polymers comprise expanded polytetrafluoroethylene, the aromatic/aliphatic polyester resins comprise polyethylene terephthalate ("PET") or poly (butylene terephthalate) ("PBT"), and the silicone rubbers comprise heat cured rubbers or silicone elastomers.

5. An article according to claim 3 wherein the biomaterial is expanded polytetrafluoroethylene.

6. An article according to claim 5 wherein the expanded polytetrafluoroethylene exhibits on the order of 10 to 300 micron internodal distance.

7. A method of preparing an implantable medical device comprising the steps of:

(a) providing an implantable device comprising a rigid, porous biomaterial providing a surface, wherein the biomaterial is porous in that it provides channels or passages extending through the biomaterial and of sufficient dimensions to permit the growth of capillaries therethrough;

(b) contacting the surface with adhesion molecules selected from the group consisting of fibronectin, laminin, collagen, and active peptide domains thereof, the adhesion molecules bearing one or more latent photoreactive groups selected from the group consisting of photoreactive aryl ketones, azides, diazirines, ketenes and diazo compounds; and (c) activating the photoreactive groups in order to immobilize the adhesion molecules by binding the adhesion molecules to each other or to the surface in an amount suitable to promote capillary endothelialization of the device in vivo.

8. A method of using an implantable medical device comprising the steps of:

(a) providing an implantable device comprising a rigid, porous biomaterial providing a surface, wherein the biomaterial is porous in that it provides channels or passages extending through the biomaterial and of sufficient dimensions to permit the growth of capillaries therethrough;

(b) contacting the surface with adhesion molecules selected from the group consisting of fibronectin, laminin, collagen, and active peptide domains thereof, the adhesion molecules bearing one or more latent photoreactive groups selected from the group consisting of photoreactive aryl ketones, azides, diazirines, ketenes and diazo compounds; and (c) activating the photoreactive groups in order to immobilize the adhesion molecules by binding the adhesion molecules to each other or to the surface; and (d) implanting the device in contact with bodily tissues or fluids in order to promote capillary endothelialization of the device by the growth of capillary endothelial cells into the porosity of the biomaterial in vivo.

9. An implantable medical device prepared by a process comprising the steps of:

(a) providing an implantable device comprising a rigid, porous biomaterial providing a surface, wherein the biomaterial is porous in that it provides channels or passages extending through the biomaterial and of sufficient dimensions to permit the growth of capillaries therethrough;

(b) contacting the surface with adhesion molecules selected from the group consisting of fibronectin, laminin, collagen, and active peptide domains thereof, the adhesion molecules bearing one or more latent photoreactive groups selected from the group consisting of photoreactive aryl ketones, azides, diazirines, ketenes and diazo compounds; and (c) activating the photoreactive groups in order to immobilize the adhesion molecules by binding the adhesion molecules to each other or to the surface in an amount suitable to promote capillary endothelialization of the device in vivo.

10. An article according to claim 2 wherein the adhesion molecule comprises fibronectin and active peptide domains thereof.

11. An article according to claim 2 wherein the adhesion molecule comprises laminin and active peptide domains thereof.

12. An article according to claim 2 wherein the adhesion molecule comprises collagen and active peptide domains thereof.

13. An article according to claim 2 wherein the photoreactive groups comprise aryl ketones selected from the group consisting of acetophenone and benzophenone.

14. An article according to claim 3 wherein the article is in the form of a vascular graft.

15. A method according to claim 7 wherein the biomaterial provides pores having an average diameter from about 5 microns to about 1 mm.

16. A method according to claim 15 wherein the biomaterial is selected from the group consisting of tetrafluoroethylene polymers, aromatic/aliphatic polyester resins, polyurethanes, and silicone rubbers.

17. A method according to claim 16 wherein the tetrafluoroethylene polymers comprise expanded polytetrafluoroethylene, the aromatic/aliphatic polyester resins comprise polyethylene terephthalate ("PET") or poly (butylene terephthalate) ("PBT"), and the silicone rubbers comprise heat cured rubbers or silicone elastomers.

18. A method according to claim 17 wherein the biomaterial is expanded polytetrafluoroethylene.

19. A method according to claim 18 wherein the expanded polytetrafluoroethylene exhibits on the order of 10 to 300 micron internodal distance.

20. A method according to claim 15 wherein the adhesion molecule comprises fibronectin and active peptide domains thereof.

21. A method according to claim 15 wherein the adhesion molecule comprises laminin and active peptide domains thereof.

22. A method according to claim 15 wherein the adhesion molecule comprises collagen and active peptide domains thereof.

23. A method according to claim 15 wherein the photoreactive groups comprise aryl ketones selected from the group consisting of acetophenone and benzophenone.

24. A method according to claim 16 wherein the article is in the form of a vascular graft.

25. A method according to claim 8 wherein the biomaterial provides pores having an average diameter from about 5 microns to about 1 mm.

26. A method according to claim 25 wherein the biomaterial is selected from the group consisting of tetrafluoroethylene polymers, aromatic/aliphatic polyester resins, polyurethanes, and silicone rubbers.

27. A method according to claim 26 wherein the tetrafluoroethylene polymers comprise expanded polytetrafluoroethylene, the aromatic/aliphatic polyester resins comprise polyethylene terephthalate ("PET") or poly (butylene terephthalate) ("PBT"), and the silicone rubbers comprise heat cured rubbers or silicone elastomers.

28. A method according to claim 27 wherein the biomaterial is expanded polytetrafluoroethylene.

29. An article according to claim 28 wherein the expanded polytetrafluoroethylene exhibits on the order of 10 to 300 micron internodal distance.

30. A method according to claim 25 wherein the adhesion molecule comprises fibronectin and active peptide domains thereof.

31. A method according to claim 25 wherein the adhesion molecule comprises laminin and active peptide domains thereof.

32. A method according to claim 25 wherein the adhesion molecule comprises collagen and active peptide domains thereof.

33. A method according to claim 25 wherein the photoreactive groups comprise aryl ketones selected from the group consisting of acetophenone and benzophenone.

34. A method according to claim 26 wherein the article is in the form of a vascular graft.

35. A device according to claim 9 wherein the biomaterial provides pores having an average diameter from about 5 microns to about 1 mm.

36. A device according to claim 35 wherein the biomaterial is selected from the group consisting of tetrafluoroethylene polymers, aromatic/aliphatic polyester resins, polyurethanes, and silicone rubbers.

37. A device according to claim 36 wherein the tetrafluoroethylene polymers comprise expanded polytetrafluoroethylene, the aromatic/aliphatic polyester resins comprise polyethylene terephthalate ("PET") or poly (butylene terephthalate) ("PBT"), and the silicone rubbers comprise heat cured rubbers or silicone elastomers.

38. A device according to claim 37 wherein the biomaterial is expanded polytetrafluoroethylene.

39. A device according to claim 38 wherein the expanded polytetrafluoroethylene exhibits on the order of 10 to 300 micron internodal distance.

40. A device according to claim 35 wherein the adhesion molecule comprises fibronectin and active peptide domains thereof.

41. A device according to claim 35 wherein the adhesion molecule comprises laminin and active peptide domains thereof.

42. A device according to claim 35 wherein the adhesion molecule comprises collagen and active peptide domains thereof.

43. A device according to claim 35 wherein the photoreactive groups comprise aryl ketones selected from the group consisting of acetophenone and benzophenone.

44. A device according to claim 36 wherein the article is in the form of a vascular graft.

* * * * *

UNITED STATES PATENT AND TRADEMARK OFFICE
CERTIFICATE OF CORRECTION

PATENT NO. : 5,744,515
DATED : April 28, 1998
INVENTOR(S) : Clapper

It is certified that error appears in the above-identified patent and that said Letters Patent is hereby corrected as shown below:

Column 10, line 31, replace "$10^{-}{}_{18}$" with --$10^{-18}$--.

Column 20, line 30, replace "An article" with --A method--.

Signed and Sealed this

Twenty-sixth Day of January, 1999

Attest:

*Attesting Officer*

*Acting Commissioner of Patents and Trademarks*

UNITED STATES PATENT AND TRADEMARK OFFICE
Certificate

Patent No. 5,744,515                                                Patented: April 28, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David L. Clapper, Shorewood, MN (US); and Stuart K. Williams, Tucson, AZ (US).

Signed and Sealed this Thirteenth Day of June 2006.

VASU JAGANNATHAN
*Supervisory Patent Examiner*
Art Unit 1714